US011406463B2

(12) United States Patent
Marshall et al.

(10) Patent No.: US 11,406,463 B2
(45) Date of Patent: Aug. 9, 2022

(54) CAMERA CONTROL

(71) Applicant: CMR SURGICAL LIMITED, Cambridge (GB)

(72) Inventors: Keith Marshall, Cambridge (GB); Rebecca Anne Cuthbertson, Cambridge (GB); Gordon Thomas Deane, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 736 days.

(21) Appl. No.: 16/281,194

(22) Filed: Feb. 21, 2019

(65) Prior Publication Data
US 2019/0262089 A1   Aug. 29, 2019

(30) Foreign Application Priority Data

Feb. 23, 2018  (GB) ..................... 1802992

(51) Int. Cl.
*A61B 1/00* (2006.01)
*A61B 1/045* (2006.01)
(Continued)

(52) U.S. Cl.
CPC .......... *A61B 34/37* (2016.02); *A61B 1/00149* (2013.01); *A61B 1/045* (2013.01);
(Continued)

(58) Field of Classification Search
CPC ......... A61B 34/37; A61B 34/30; A61B 34/74; A61B 34/35; A61B 1/00149; A61B 1/045;
(Continued)

(56) References Cited

U.S. PATENT DOCUMENTS

2003/0144649 A1   7/2003  Ghodoussi et al.
2006/0178559 A1*  8/2006  Kumar ................... G16H 40/63
                                                          600/109
(Continued)

FOREIGN PATENT DOCUMENTS

WO   2013018936 A1   2/2013
WO   2017031132 A1   2/2017
(Continued)

OTHER PUBLICATIONS

Notification of Transmittal of the International Search Report and the Written Opinion of the International Searching Authority from corresponding PCT/GB2019/050455 dated May 20, 2019.
(Continued)

*Primary Examiner* — Timothy J Neal
*Assistant Examiner* — William B Chou
(74) *Attorney, Agent, or Firm* — Lando & Anastasi, LLP (57) ABSTRACT

A master-slave system that includes a first manipulator supporting a first end effector; a second manipulator supporting a second end effector; an input device configured to concurrently receive from a hand of an operator a first movement command to effect a desired movement of the first end effector and a second movement command to effect a desired movement of the second end effector; and a processor configured to determine a desired movement of the first and the second end effectors in response to the first and second movement commands received from the input device respectively.

18 Claims, 8 Drawing Sheets

(51) Int. Cl.
A61B 34/37 (2016.01)
A61B 34/00 (2016.01)
A61B 34/30 (2016.01)
*A61B 90/00* (2016.01)
*A61B 90/50* (2016.01)
*A61B 34/35* (2016.01)

(52) U.S. Cl.
CPC .............. *A61B 34/30* (2016.02); *A61B 34/74* (2016.02); *A61B 34/35* (2016.02); *A61B 90/361* (2016.02); *A61B 90/50* (2016.02); *A61B 2034/301* (2016.02); *A61B 2034/302* (2016.02); *A61B 2090/373* (2016.02)

(58) Field of Classification Search
CPC ........ A61B 2034/301; A61B 2034/302; A61B 90/361; A61B 90/50; A61B 2090/373
See application file for complete search history.

(56) References Cited

U.S. PATENT DOCUMENTS

| | | | |
|---|---|---|---|
| 2010/0300230 A1* | 12/2010 | Helmer | B25J 9/106 74/469 |
| 2011/0276058 A1* | 11/2011 | Choi | B25J 9/1671 606/130 |
| 2013/0211590 A1 | 8/2013 | Diolaiti et al. | |
| 2013/0267964 A1 | 10/2013 | Rogers et al. | |
| 2013/0325031 A1 | 12/2013 | Schena et al. | |
| 2016/0270867 A1 | 9/2016 | Scholan | |
| 2017/0128145 A1 | 5/2017 | Hasser et al. | |
| 2017/0189126 A1 | 7/2017 | Weir | |

FOREIGN PATENT DOCUMENTS

| | | |
|---|---|---|
| WO | 2017055381 A1 | 4/2017 |
| WO | 2017098259 A1 | 6/2017 |

OTHER PUBLICATIONS

United Kingdom Search Report from corresponding United Kingdom Application No. GB1802992.6 dated Aug. 1, 2018.
Japanese Notification of Reasons for Rejection from corresponding Japanese Application No. 2020-544397 dated Mar. 15, 2022.

* cited by examiner

CAMERA CONTROL

CROSS-REFERENCE TO RELATED APPLICATION

This application claims the benefit under 35 U.S.C. § 119 of United Kingdom Patent Application No. 1802992.6 filed on Feb. 23, 2018 which is hereby incorporated herein by reference in its entirety for all purposes.

BACKGROUND

Typically, in robotic master-slave systems, an operator controls the movements of a number teleoperated tools using one or more input devices. Consequently, the operator can control the tools without needing to be in the same location as the worksite in which the tools are being manipulated. Image capture devices, such as cameras, and a display for displaying a view of the captured images may be included to provide the operator with a view of the worksite. Some applications of robotic master-slave systems include assembly, maintenance or exploration in hazardous environments (e.g. underwater, nuclear or chemical plant), and minimally invasive surgical systems.

In surgical systems in particular, the operator(s) who may be a surgeon, an assistant, a student or a combination thereof can remotely manipulate a number of remote tools (such as surgical instruments) supported by a number of robotic manipulators by manipulating a number of input devices at an operator's console (e.g. a surgeon's console). As well as surgical instruments, the robotic manipulators may support image capture devices, such as endoscopes, to provide the operator with a view of the remote surgical site on a display at the surgeon's console.

During surgery, the surgeon manipulates an input device to control the movement of the surgical instrument at the surgical site. Typically, an endoscope used in the procedure is controlled by a camera assistant who manipulates the endoscope in response to verbal instructions received from the surgeon to provide the surgeon with a desired view of the surgical site. Alternatively, the surgeon may use the same input device being used to manipulate the surgical instrument to control the endoscope by entering an endoscope mode in which operation of the surgical instrument is halted and the instrument is locked in place, the input device is then disassociated from the instrument and is associated with the endoscope to control the movement of the endoscope. Once the endoscope has been manipulated and the desired viewpoint is obtained, the endoscope mode described above is exited, the input device is disassociated from the endoscope and re-associated with the instrument so that the surgeon can resume operation of the instrument.

However, such methods of controlling the endoscope are inefficient at best. Specifically, the method in which a camera assistant controls the endoscope can lead to delays and errors (e.g. it is possible for the surgeon to become disorientated by the movement of the endoscope frame of reference with respect to the surgeon's position). In the method in which the surgeon uses the input device to control the endoscope, the surgeon needs to stop the surgical procedure before the surgeon can manipulate the endoscope to change his/her viewpoint of the surgical site. In contrast, during normal open surgery the surgeon can move their head in response to a need or stimulus to change their viewpoint of the surgical site while carrying on with the procedure at the same time.

There is, therefore, a need for an improved master-slave system which would allow a surgeon to more intuitively and comfortably change their view of the surgical site while at the same time being able to carry on with the procedure at hand.

SUMMARY OF THE INVENTION

Accordingly, the present invention provides a master-slave system comprising: a first manipulator supporting a first end effector; a second manipulator supporting a second end effector; an input device configured to concurrently receive from a hand of an operator a first movement command to effect a desired movement of the first end effector and a second movement command to effect a desired movement of the second end effector; and a processor configured to determine a desired movement of the first and the second end effectors in response to the first and second movement commands received from the input device.

The input device may further comprise a body for being held by an operator. The body may be configured to be gripped by a single hand of the operator.

The input device may further comprise a first input for receiving the first movement command to effect a desired movement of the first end effector.

The processor may be configured to operate in a plurality of modes including: an engaged mode, wherein the processor operatively couples the input device with the second end effector; a disengaged mode, wherein the processor operatively decouples the input device from the second end effector; an operational mode, wherein the processor operatively couples the first input with the first end effector; and a selection mode, wherein the processor operatively decouples the first input from the first end effector.

The processor may further be configured to operate in the disengaged mode in response to a signal received from a clutch input. The processor may further be configured to operate in the operational mode in response to receiving a signal from a second input. The processor may further be configured to concurrently operate in the disengaged mode and the selection mode when the processor enters the disengaged mode.

The input device may further be configured to receive the second movement command to effect a desired movement of the second end effector when the processor is operating in the engaged mode.

The first input may be configured to receive the first movement command to effect a desired movement of the first end effector when the processor is operating in the operational mode. The first input may further be configured to select a third end effector for association with the input device when the processor is operating in the selection mode. The input device may further be configured to receive a third movement command to effect a desired movement of the third end effector in response to selection of the third end effector by the first input.

The input device may further comprise a drive mechanism coupled to the first input, the drive mechanism being configured to apply a force to the first input for providing force feedback to the operator. The input device may further comprise a force sensor configured to sense a force applied to the first input for determining that a command is being received at the first input from the operator. The first input device may further comprise a capacitive sensor configured to sense when the operator is touching the first input for determining that a command is being received at the first input from the operator. The input device may further comprise a position sensor configured to sense the position of the first input relative to the body for determining that a command is being received at the first input from the operator.

The processor may further be configured to effect movement of the first end effector in accordance with the determined desired movement of the first end effector. The processor may further be configured to effect movement of the second end effector in accordance with the determined desired movement of the second end effector.

The first end effector may have multiple degrees of freedom and the processor may be configured to selectively associate at least one of the degrees of freedom of the first end effector with the first input and to effect movement of the at least one of the degrees of freedom of the first end effector in response to movement of the first input.

The first end effector may comprise an image capture device for capturing an image of a worksite. The image capture device may be an endoscope. The master-slave system may further comprise a display for displaying the captured image.

The processor may further be configured to effect movement of the first end effector according to movement of the first input with respect to an operator selected frame of reference. The operator selected frame of reference may be fixed to the input device. The operator selected frame of reference may be fixed to the display. The processor may further be configured to continuously update a mapping between an input device frame of reference and a second end effector frame of reference and to continuously update a mapping between a first input frame of reference and a first end effector frame of reference such that movements of the first and second end effectors as displayed on the display correspond to the movements of the first input and the input device respectively.

BRIEF DESCRIPTION OF THE FIGURES

The present invention will now be described by way of example with reference to the accompanying drawings in which:

FIG. 5b shows a perspective view of the input device of FIG. 5a;

DETAILED DESCRIPTION

Figure 1:
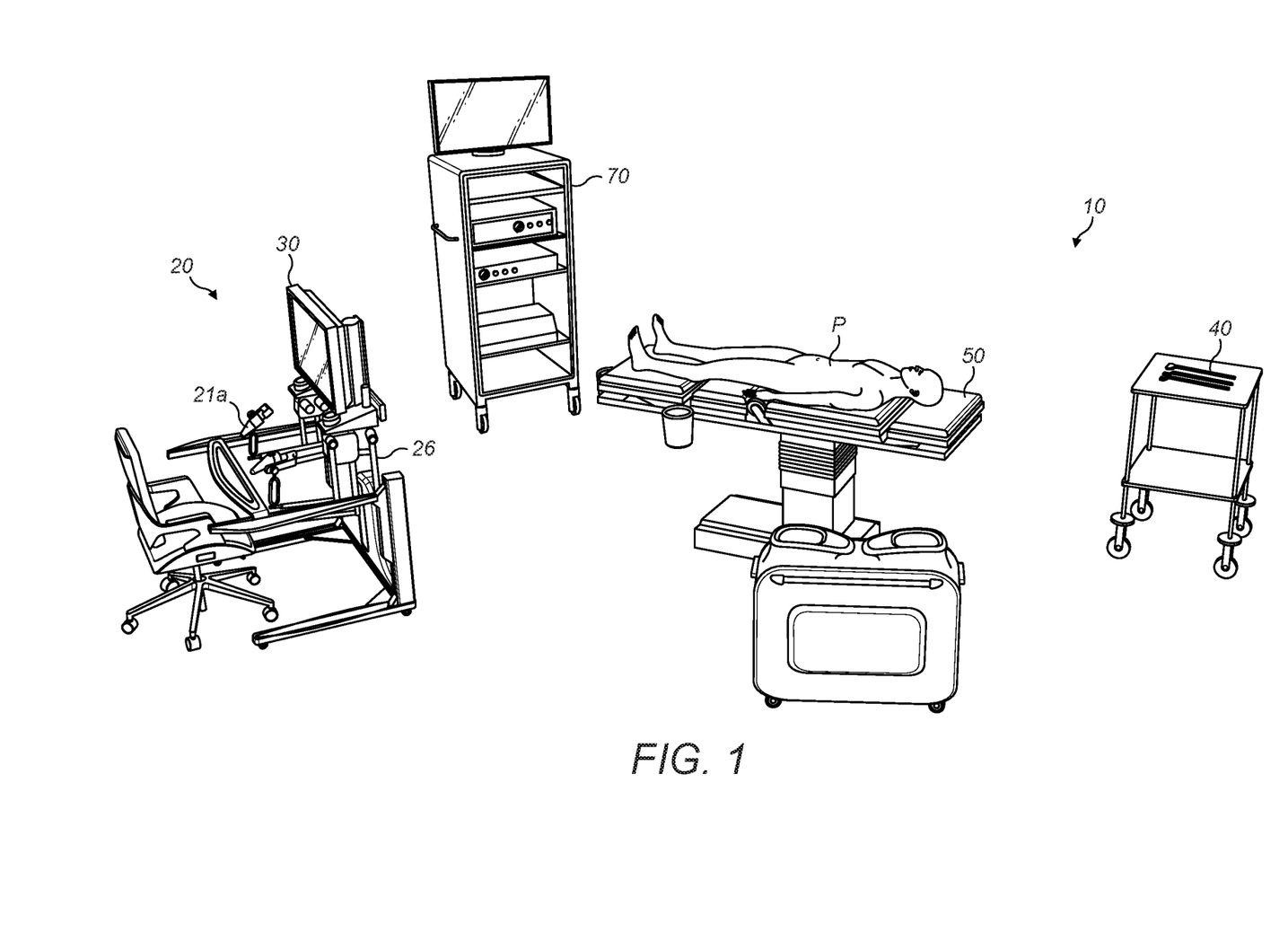
FIG. 1 shows a master-slave system.

FIG. 1 shows a master-slave system 10 in an exemplary configuration as a surgical system. The system 10 includes a patient table 50, a cart 70, and an operator console 20. The operator console 20 allows an operator O (shown in FIG. 7) to carry out a surgical procedure on patient P by remotely manipulating one or more robotic manipulator(s) 80a, 80b, 80c (shown in FIG. 2) which supports a tool 40a, 40b, 40c using one or more input device(s) 21a, 21b. The operator O may, for example, be a surgeon, an assistant, or a student.

Figure 2:
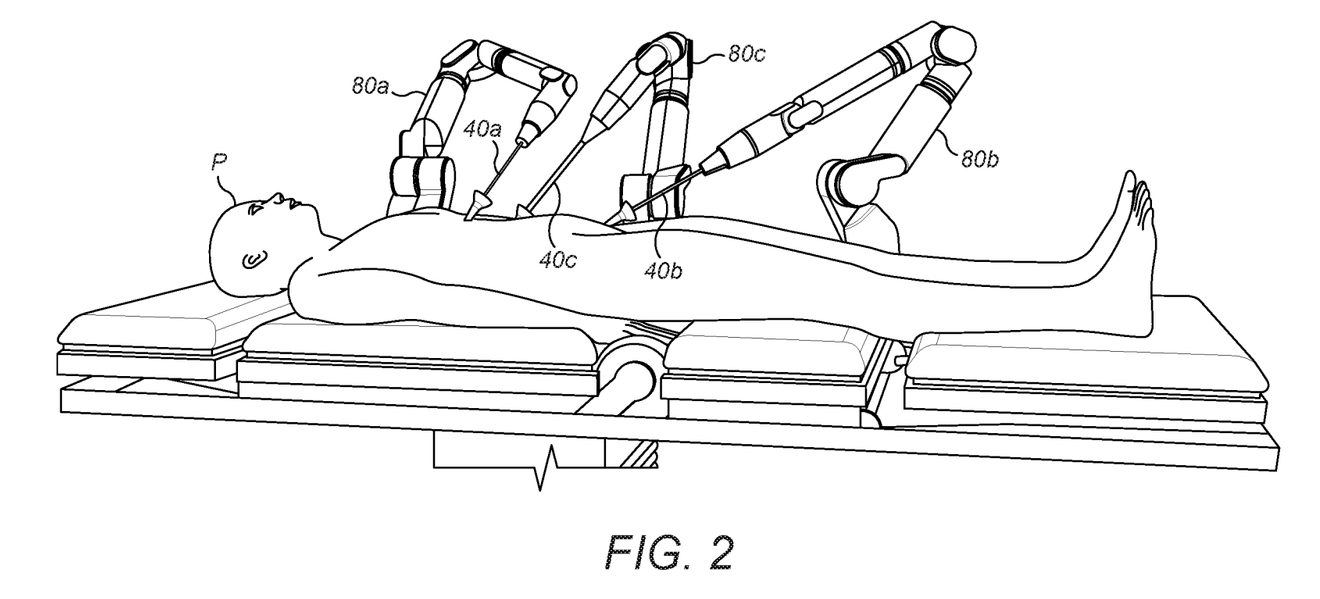
FIG. 2 shows a patient undergoing tele-surgery using a plurality of robotic manipulators each supporting a tool.
Figure 3:
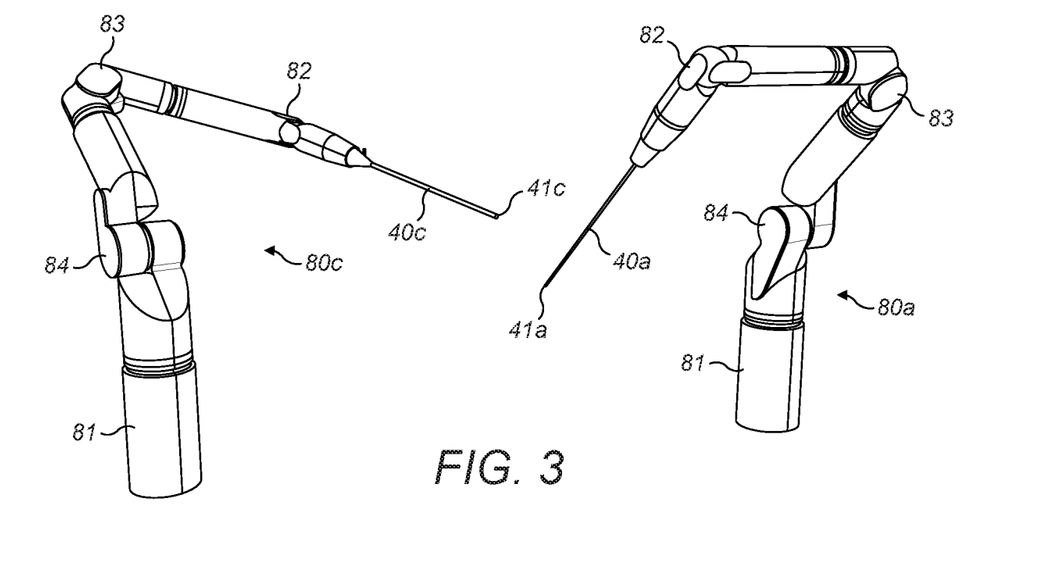
FIG. 3 shows two examples of the robotic manipulators of FIG. 2 each supporting a different tool.
Figure 6:
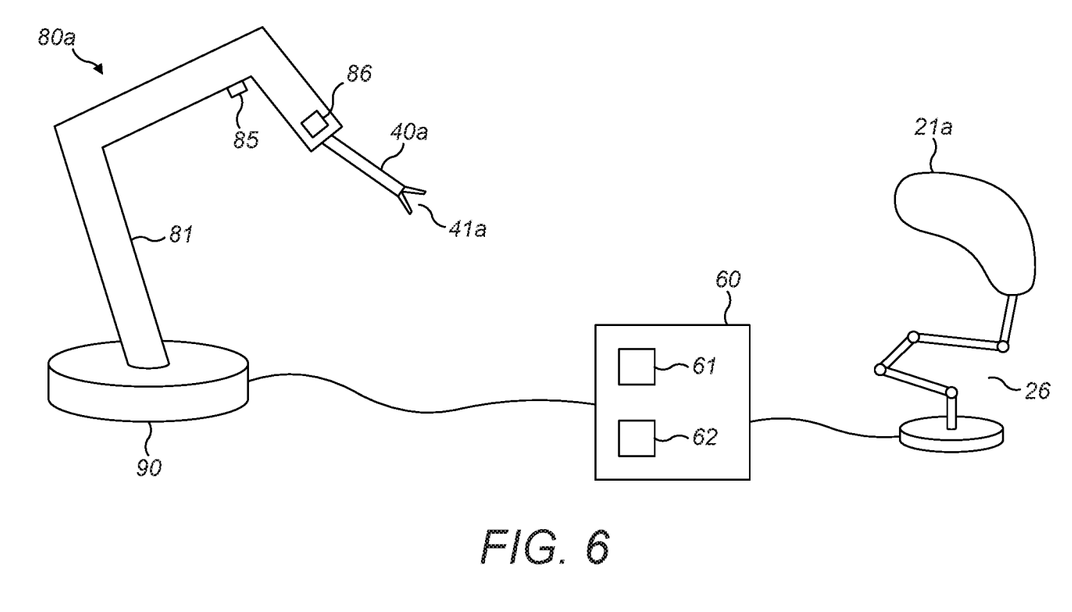
FIG. 6 shows a schematic representation of the system of FIG. 1.

Referring now to FIG. 2, the system 10 has one or more robotic manipulators 80a, 80b, 80c for supporting a variety of tools 40a, 40b, 40c. The robotic manipulator(s) 80a, 80b, 80c may be as shown in FIGS. 2, 3 and 6. The robotic manipulators 80a, 80b, 80c of FIGS. 2, 3 and 6 each have an arm 81 which extends from a base 90 (shown in FIG. 6). The arm 81 is articulated by a series of revolute joints 82, 83, 84 along its length. At the distal end of the arm 81 is a tool 40a, 40b, 40c which terminates in an end effector 41a, 41b, 41c. The end effector 41a, 41b may be a surgical instrument such as, but not limited to, smooth jaws, serrated jaws, a gripper, a pair of shears, a needle for suturing, a laser, a knife, a stapler, a cauteriser, a suctioner, pliers, a scalpel, cautery electrode, or the like. The end effector 41c may alternatively be an image capture device, such as an endoscope. The end effector 41a, 41b, 41c can be driven to move by a drive motor 86 at the distal end of the arm 81. The drive motor 86 may be coupled to the end effector 41a, 41b, 41c by cables extending along the interior of the instrument's shaft.

Whilst FIG. 3 shows a robotic manipulator 80c supporting an endoscope 41c and a robotic manipulator 80a supporting an instrument end effector 41a, it will be appreciated that each of the robotic manipulators 80a, 80b, 80c can support any of the end effectors.

Figure 4:
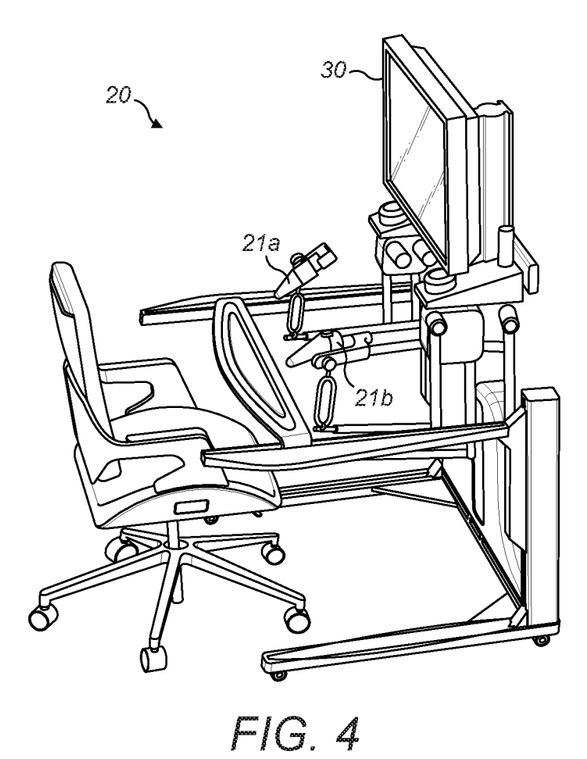
FIG. 4 shows an operator console including a display and an input device.
Figure 5A:
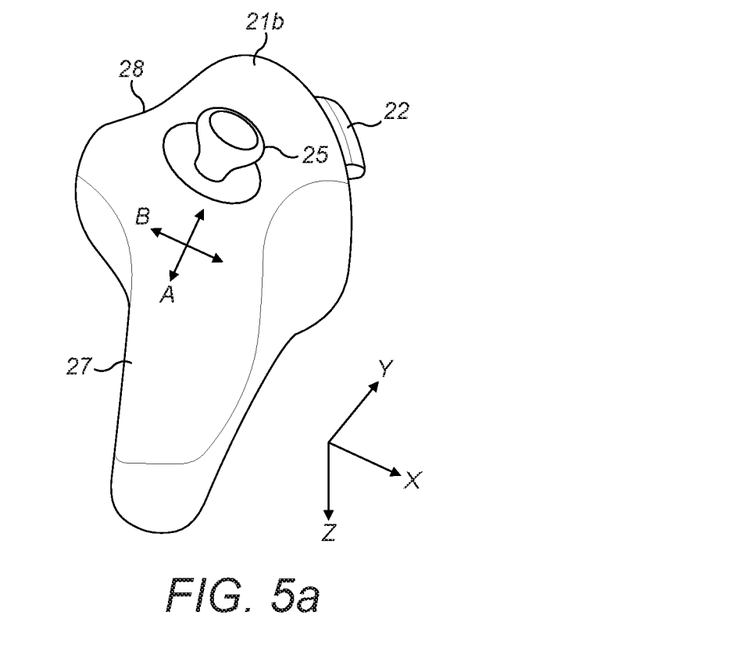
FIG. 5a shows a top view of an input device including an input and a clutch input.
Figure 5B:
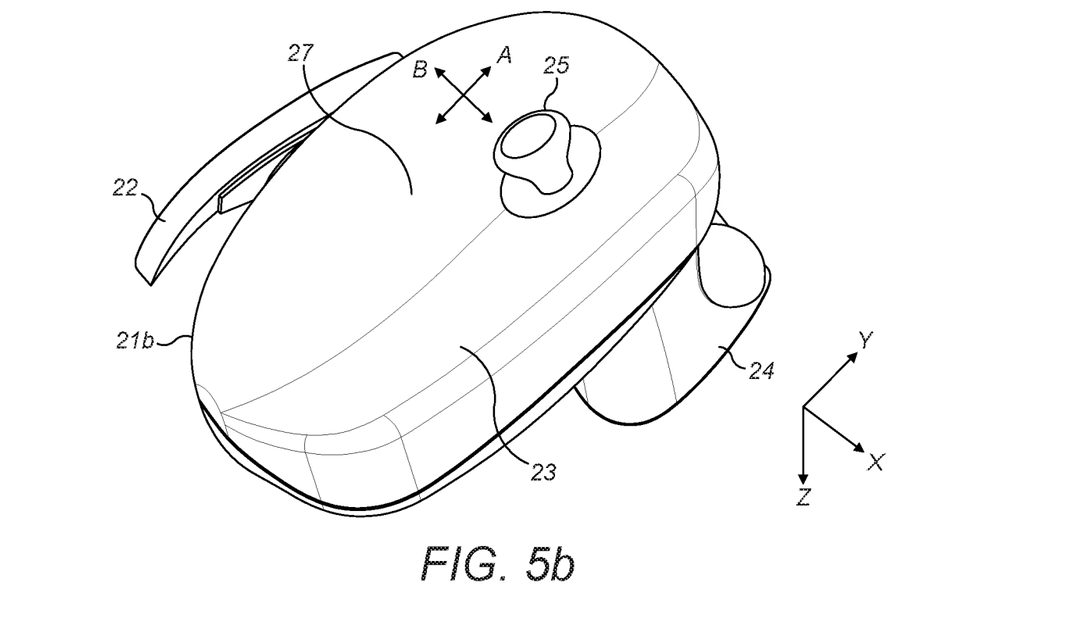

Referring now to FIG. 4, the operator console 20 includes one or more input devices 21a, 21b coupled to a linkage assembly 26 for controlling the robotic manipulator(s) 80a, 80b, 80c. The operator console 20 also includes a display 30 for providing the operator O with a view of the remote surgical worksite. The input device(s) 21a, 21b of FIGS. 4, 5a and 5b are designed to be held in a user's hand for providing three-dimensional motion input to the system 10. In some cases the input device(s) 21a, 21b may also allow the user to provide functional input to the system 10.

Whilst the above description refers to a single display device, in other examples the robotic system may comprise a plurality of display devices, or screens. The screens are suitably configured to display the view of the remote worksite as a two-dimensional image and/or as a three-dimensional image. The screens can be provided on a single operator console 20, or two or more consoles can comprise at least one screen each. This permits additional viewing screens which can be useful for allowing people other than the console operator to view the surgical worksite, for example for training.

For ease of explanation an example input device 21b will be described with reference to mutually orthogonal X, Y and Z axes indicated in FIGS. 5a and 5b. The X axis is orthogonal to the forward/rearward axis of the input device 21b. The Y axis is orthogonal to the left/right axis of the input device 21b. The Z axis is parallel to the up/down axis of the input device 21b and orthogonal to the X and the Y axes. In other words, the Z axis of the input device 21b is a line going through the body of the input device 21b from its top to its bottom surface.

The example input device 21b of FIGS. 5a and 5b is intended to be grasped in the right hand. A mirror image input device 21a could be intended for the left hand. The body 27 of the input device 21b has a head 23 and a grip 24. The grip 24 is configured to sit in the palm of the user's hand. This allows the user to place their first/index finger on a clutch input 22. The user's thumb can be placed on the opposite side of the head 23 to the clutch input 22 or alternatively the user's thumb can be placed on an input 25 on the head 23. User acceptance testing of devices of this type has established that many users naturally pick up and hold such a device in this manner, with their wrist in a neutral position and their thumb opposing their finger. This has the result that for three-dimensional motion input the user's wrist is free to move in flexion, extension, adduction and abduction.

In the input device 21b of FIGS. 5a and 5b, the clutch input 22 is shown as being a trigger lever that can rotate relative to the head 23 about an axis (not shown). The clutch input 22 could variably be termed the pince or pinch input. For a more detailed description of such a clutch input, refer to the Applicant's GB Patent Application No. GB1616086.3, entitled "Hand Controller Grip". Furthermore, in the input device 21b of FIGS. 5a and 5b, the input 25 is shown as being a thumbstick that pivots on a base and reports its position in relation to a default centre position to a control unit 60. This position signal can then be used as a further motion input and, optionally, as a functional input in the system 10. The input 25 of FIGS. 5a and 5b is designed to be manipulated with the user's thumb and typically provides a two-dimensional input.

Input 25 could be articulated in several ways. For example, the input 25 could pivot in a forward/rearward direction A about the X axis of input device 21b. The input 25 could also pivot in a left/right direction B about the Y axis of input device 21b. The input 25 could also behave as a push-button to provide an up/down movement of the input 25 along the Z axis of input device 21b.

The input 25 is positioned on the input device 21a, 21b such that it can be used in a comfortable and natural way by the user but not inadvertently actuated. The input 25 may be in an inoperable state by default, in which state any input received by the system from input 25 is ignored. The input 25 may only become operable once it has been detected that it is being engaged by a user. To do this a touch sensitive panel (not shown) could be provided on the surface of input 25 which could be engaged by the user's thumb. The touch-sensitive panel could include a capacitive sensor (not shown) to detect the presence of the user's thumb on the input 25 when the user's thumb is touching the input 25. Alternatively or additionally, haptic feedback could be provided for input 25 to detect any shaking or vibrating resulting from the user's thumb touching the input 25 to detect the presence of the user's thumb on the input 25.

Preferably, the input 25 is in an operable state by default. In this scenario to stop any inadvertent actuation of the input 25 by the user, a neutral zone could be defined within the articulation range of the input 25 which will not produce any output. For example, the input 25 may need to be pivoted in a forward/rearward direction about the X axis of input device 21a, 21b beyond a certain threshold value before an output signal is actioned and any resulting movement of an associated slave is generated in the system. Visual cues may be provided on the display 30 and/or on the input device 21a, 21b to indicate the band of input values to the input 25 which will not produce any output to the system.

A position sensor may be provided within the head 23 to sense the position of the input 25 relative to the body 27. The position sensor may be able to discriminate a range of positions of the input 25, allowing the extent to which the input 25 is pivoted or is pressed to be identified more precisely. The position sensor may be a rotational encoder or a potentiometer arranged about the rotation axis of the input 25. In addition to, or instead of, a position sensor the input device 21b may comprise a force and/or torque sensor for detecting the force applied to the input 25 and/or the torque applied to the input 25 about its pivot axis.

Additional user input interface may be provided on the head 23. For example, there may be one or more pushbuttons, rotational knobs, joysticks, rocker switches or the like.

Referring now to FIG. 6, an example robotic manipulator 80a is governed by a control unit 60. The control unit 60 receives inputs from an input device 21a, 21b and from other sources such as the linkage assembly 26 and the robotic manipulator position/force sensors 85.

The linkage assembly 26 is an articulated linkage which supports the input device 21a, 21b and permits it to be moved with six degrees of freedom. The configuration of the linkage assembly 26 can be detected by sensors on the linkage and passed to the control unit 60. In that way movement of the input device 21a, 21b can be used to control the movement of the robotic manipulator 80a. Instead of the linkage assembly 26, the input device 21a, 21b may be equipped with accelerometers which permit its position and orientation to be estimated.

The control unit 60 comprises a processor 61 which executes code stored in a non-transient form in a memory 62. On executing the code, the processor 60 determines a set of signals for commanding movement of the joints 82, 83, and 84 of the robotic manipulator 80a, and for moving the end effector 41a of the instrument 40a in dependence on the inputs from the input device 21a, 21b, the linkage assembly 26, and the manipulator position/force sensors 85. The code is configured so that the motion of the robotic manipulator 80a is essentially dictated by the inputs from the input device 21a, 21b and the linkage assembly 26. For example, in a normal operating mode (i) the attitude of the end effector 41a may be set by the attitude of the input device 21a, 21b about its rotational degrees of freedom; (ii) the position of the end effector 41a may be set by the position of the input device 21a, 21b about its translational degrees of freedom; and (iii) the configuration of the jaws of the end effector 41a may be set by the position of the clutch input 22 or input 25 relative to the body 21. For example, clutch input 22 can be used to operate the jaws of a surgical instrument end effector.

Camera Control

Furthermore, when the robotic manipulator 80c is supporting an image capture device such as an endoscope 41c, on executing the code, the processor 60 determines a set of signals for commanding movement of the joints 82, 83, and 84 of the robotic manipulator 80c, and for moving the endoscope 41c in dependence on the inputs from the input 25 and the position/force sensors of the input device 21a, 21b. For example, in a normal operating mode (i) the up/down position of the distal end of the endoscope 41c may be set by the position of the input 25 of a first input device 21a about its default position in a forward/rearward direction A; (ii) the left/right position of the distal end of the endoscope 41c may be set by the position of the input 25 of the first input device 21a about its default position in a left/right direction B; (iii) the zoom level of the endoscope 41c may be set by the position of the input 25 of a second input device 21b about its default position in a forward/rearward direction A; and (iv) the rotation of the distal end of the endoscope 41c may be set by the position of the input 25 of the second input device 21b about its default position in a left/right direction B. It is to be noted that the input devices 21a and 21b could be mapped conversely to that described above so that the first input device 21a controls the rotation and zoom level of the endoscope 41c and the second input device 21b controls the up/down and left/right movement of the distal end of the endoscope 41c. Alternatively, a single input device 21a or 21b is used to control all of the above described degrees of freedom of the endoscope 41c. As before, (i) the up/down position of the distal end of the endoscope 41c may be set by the position of the input 25 of a first input device 21a about its default position in a forward/rearward direction A; (ii) the left/right position of the distal end of the endoscope 41c may be set by the position of the input 25 of the first input device 21a about its default position in a left/right direction B. At this point the operator O may press the input 25 to switch from controlling the up/down and left/right directions of motion of the distal end of the endoscope 41c to controlling the rotation and zoom level of the endoscope 41c. Once the switch has been made (iii) the zoom level of the endoscope 41c may be set by the position of the input 25 of the first input device 21a about its default position in a forward/rearward direction A; and (iv) the rotation of the endoscope 41c may be set by the position of the input 25 of the first input device 21a about its default position in a left/right direction B. Alternatively, the operator O may choose the mapping between the forward/rearward and left/right movements of the input 25 and the up/down, left/right, rotation and zoom level of the endoscope 41c according to their own preference. In other words, the operator O can select which degrees of freedom of the input 25 to map onto which degrees of freedom of the endoscope 41c. This will be described in more detail below. Thus, the operator O of system 10 is able to use a single input device 21a, 21b to concurrently control the instrument end effector 41a, 41b and the endoscope 41c without the need to halt either the manipulation of the instrument end effector 41a, 41b or the endoscope 41c.

When the robotic manipulator 80c is supporting an image capture device such as endoscope 41c, on executing the code, the processor 60 may determine the set of signals for moving the endoscope 41c in dependence on the inputs from the input 25 and the position/force sensors of the input device 21a, 21b using velocity control such that the speed with which the endoscope 41c is moved in a desired direction may also be controlled. For example, the input 25 may be configured such that it is biased to return to a neutral position. In a normal operating mode (i) the speed with which the distal end of the endoscope 41c is moved in an up/down direction may be set by the position of the input 25 of a first input device 21a about its default neutral position in the forward/rearward direction A; (ii) the speed with which the distal end of the endoscope 41c is moved in a left/right direction may be set by the position of the input 25 of the first input device 21a about its default neutral position in a left/right direction B; (iii) the speed with the zoom level of the endoscope 41c is changed may be set by the position of the input 25 of a second input device 21b about its default neutral position in a forward/rearward direction A; and (iv) the speed with which the rotation of the distal end of the endoscope 41c is effected may be set by the position of the input 25 of the second input device 21b about its default neutral position in a left/right direction B. Put another way, when the operator O wishes to move the endoscope 41c in a desired way, they will push the input 25 of the relevant input device 21a, 21b in one of the appropriate directions described above. How far they push the input 25 in the appropriate direction away from the neutral position, determines how fast the endoscope 41c moves in the desired way. Once the operator O releases the input 25, the endoscope 41c stops moving and the input 25 returns to its neutral position. It is to be noted that the input devices 21a and 21b could be mapped conversely to that described above so that the first input device 21a controls the rotation and zoom level of the endoscope 41c and the second input device 21b controls the up/down and left/right movement of the distal end of the endoscope 41c.

Alternatively, a single input device 21a or 21b is used to control all of the above described degrees of freedom of the endoscope 41c using velocity control. As before, the input 25 is configured such that it is biased to return to a neutral position; (i) the speed with which the distal end of the endoscope 41c is moved in the up/down direction may be set by the position of the input 25 of a first input device 21a about its default neutral position in a forward/rearward direction A; (ii) the speed with which the distal end of the endoscope 41c is moved in the left/right direction may be set by the position of the input 25 of the first input device 21a about its default neutral position in a left/right direction B. At this point the operator O may press the input 25 to switch from controlling the up/down and left/right directions of motion of the distal end of the endoscope 41c to controlling the rotation and zoom level of the endoscope 41c. Once the switch has been made (iii) the speed with which the zoom level of the endoscope 41c is changed may be set by the position of the input 25 of the first input device 21a about its default neutral position in a forward/rearward direction A; and (iv) the speed with which the rotation of the endoscope 41c is effected may be set by the position of the input 25 of the first input device 21a about its default neutral position in a left/right direction B. Alternatively, the operator O may choose the mapping between the forward/rearward and left/right movements of the input 25 and the up/down, left/right, rotation and zoom level of the endoscope 41c according to their own preference. In other words, the operator O can select which degrees of freedom of the input 25 to map onto which degrees of freedom of the endoscope 41c. This will be described in more detail below. Thus, the operator O of system 10 is able to use a single input device 21a, 21b to concurrently control the instrument end effector 41a, 41b and the endoscope 41c without the need to halt either the manipulation of the instrument end effector 41a, 41b or the endoscope 41c.

In this way, the operator O of system 10 can reposition the endoscope 41c to capture a different view of the worksite during a procedure without needing to stop the procedure. The endoscope 41c can thus be regarded as another slave end effector.

Master-Slave Relationship

Figure 7:
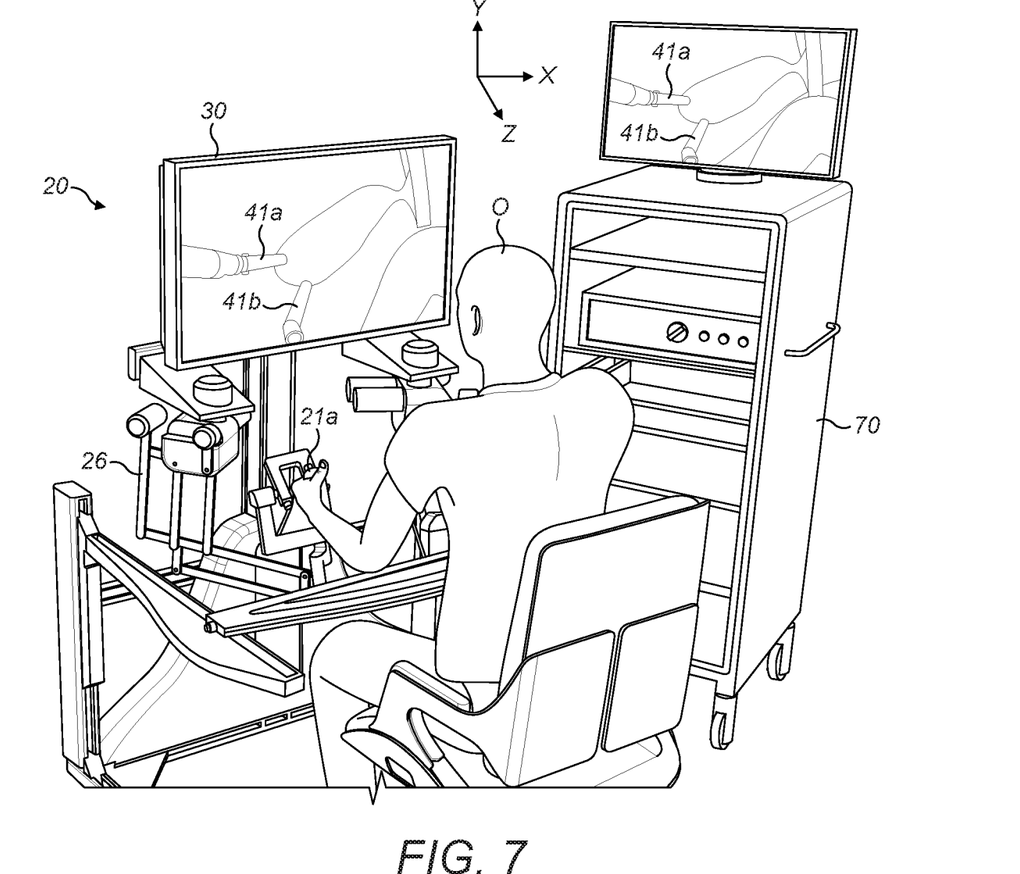
FIG. 7 shows an operator using the operator console of FIG. 4.

Referring to FIG. 7, the operator O carrying out a procedure using the operator console 20 uses the input device(s) 21a, 21b (the masters) to control the movements of the one or more remote tools 40a, 40b, 40c (the slaves). The operator O can view the worksite via the display 30. Instrument end effectors 41a and 41b supported on robotic manipulators 80a and 80b are manipulated to effect positional and orientational movements in response to movement and functional inputs on their respective associated input device(s) 21a, 21b. During the procedure, images of the instrument end effectors 41a, 41b together with the surgical site are captured by the endoscope 41c supported on robotic manipulator 80c and are displayed on the display 30 so that the operator O can see the responsive movements and actions of the instrument end effectors 41a, 41b as they control such movements and actions using the input device(s) 21a, 21b.

Advantageously, the control unit 60 establishes a relationship between input device 21a, 21b and the instrument end effector 41*a*, 41*b* associated with it as viewed in the captured image being displayed on display 30, in which relationship the orientation and position of the instrument end effector 41*a* or 41*b* as displayed to the operator O in the image follows and corresponds to the orientation and position of the associated input device 21*a* or 21*b* as manipulated by the operator's hand. By mapping the orientation and position of the associated instrument end effector 41*a* or 41*b* onto the input device's orientation and position, controlling the movement of the instrument end effector 41*a* or 41*b* can be performed in a more intuitive manner than in the case where the movement of the instrument end effector 41*a* or 41*b* as displayed in the image were not mapped onto the movement of the operator's hand.

Additionally, the control unit 60 establishes a relationship between input 25 and the endoscope 41*c* associated with it, in which relationship the orientation and position of the endoscope 41*c* follows and corresponds to the orientation and position of the associated input 25 as manipulated by the operator's hand. By thus mapping the orientation and position of the associated endoscope 41*c* onto the input's orientation and position, controlling the movement of the endoscope 41*c* can be performed in a more intuitive manner than in the case where the movement of the endoscope 41*c* were not mapped onto the movement of the input 25.

The control unit 60 effects control between an input device 21*a*, 21*b* and an instrument end effector 41*a*, 41*b* by mapping the input device's position and orientation in an input device Cartesian coordinate reference system (input frame) with the position and orientation of the instrument end effector 41*a* or 41*b* in a camera Cartesian coordinate reference system (camera frame). Accordingly, during operation, the instrument end effector's position and orientation within the camera frame is mapped to the position and orientation of the input device 21*a*, 21*b* in the input frame and the instrument end effector 41*a* or 41*b* is effected to move to a new position/orientation in the camera frame which corresponds to the current position and orientation of the input device 21*a*, 21*b* in the input frame.

In some cases, the control unit 60 effects control between input 25 and the endoscope 41*c* by mapping the input's position and orientation with respect to the input device 21*a*, 21*b* in an input Cartesian coordinate reference system (input frame) with the position and orientation of the endoscope 41*c* in the camera frame. Accordingly, during operation the endoscope 41*c* is effected to move to a new position/orientation in the camera frame which corresponds to the current position and orientation of the input 25 in the input frame.

Alternatively, the control unit 60 effects control between input 25 and the endoscope 41*c* using velocity control by mapping the input's position about its default neutral position with respect to the input device 21*a*, 21*b* in an input frame with the direction and speed of motion of the endoscope 41*c* in the camera frame. Accordingly, during operation, the endoscope 41*c* is effected to move in a new direction and at a desired speed in the camera frame which corresponds to the position of the input 25 about its default neutral position in the input frame.

Advantageously, the user can disengage the input device 21*a*, 21*b* and move it to a more ergonomic position and or orientation. Upon re-engagement of the input device 21*a*, 21*b*, the mapping between the input frame and the camera frame is updated. Thus, the master frame of reference can be changed and also vary between the input device 21*a* and the input device 21*b*. Additionally, this update of the mapping between the master (input device 21*a*, 21*b*) and the slave (end effector 41*a*, 41*b*, 41*c*) results in the movement commands given via the input device 21*a*, 21*b* to produce the expected motion of the slave as displayed to the operator O on display 30.

It will be appreciated that, should the image capture device's position change, the orientation and position of the instrument end effector 41*a* or 41*b* in the viewed image could also change. Consequently, and advantageously, the relationship in which the movement of the instrument end effector 41*a*, 41*b* is mapped onto the movement of the input device 21*a*, 21*b* is again established after such a positional change by the image capture device. This will enhance the operator's intuitive "feel" when performing a procedure as this continuous update of the mapping between the master and the slave would result in the movement commands given via the input device 21*a*, 21*b* to produce the expected motion of the slave as displayed to the operator O.

Additionally, to provide the operator O with an improved and more intuitive response between the movement of the input 25 and the movement of the distal end of the endoscope 41*c*, the control unit 60 determines and effects a desired position and orientation of the distal end of the endoscope 41*c* based on the position and orientation of the input 25 by means of the input frame relative to a frame of reference of the operator's preference. This concept is illustrated in FIGS. 8*a* and 8*b* and is described below.

Figure 8A:
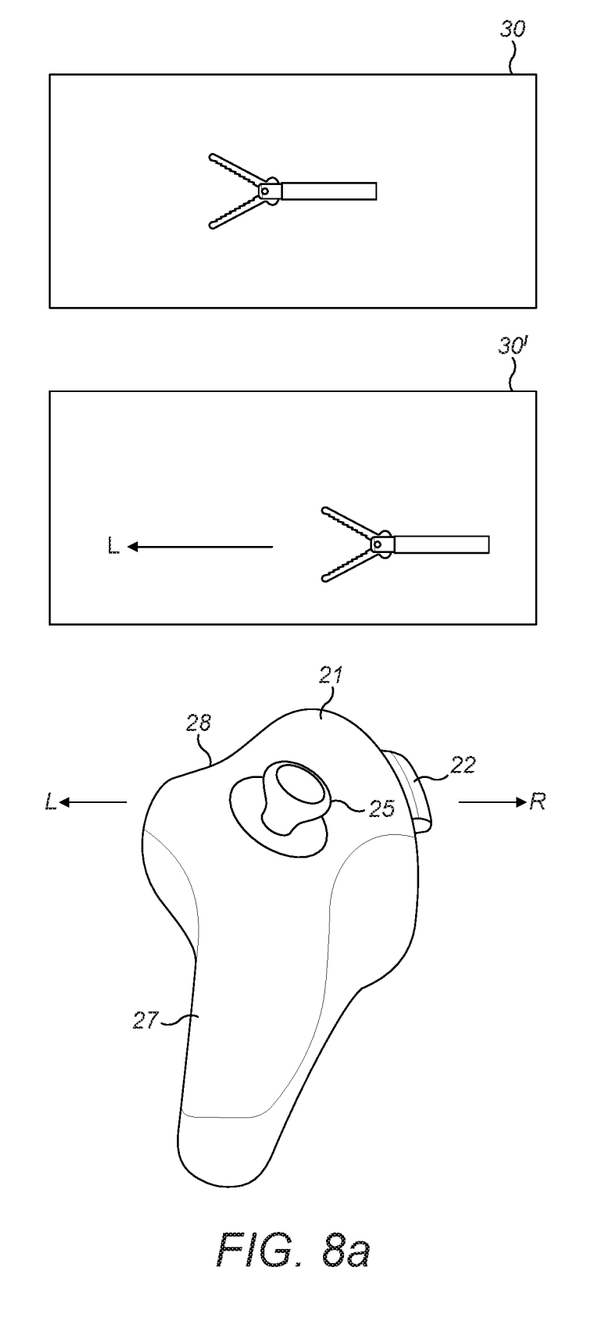
FIG. 8a shows a view of the input of FIG. 5a with its operator selected frame of reference fixed to the input of FIG. 4.

FIG. 8*a* illustrates an example in which the operator O is holding the input device 21*a* such that it is pointed squarely at the screen of display 30. The operator O can choose to set their preferred frame of reference to be the same as that of the input device 21*a* (i.e. the input frame). In this example, before the input 25 is manipulated, the operator O can see the instrument end effector 41*a* as shown on display 30. However, once the input 25 is moved left in respect to the body of the input device 21, in the direction indicated by letter L in FIG. 8*a*, the distal end of the endoscope 41*c* is also moved leftwards, resulting in the displayed image of the instrument end effector 41*a* to shift to the right side of the captured image as shown on display 30'.

Figure 8B:
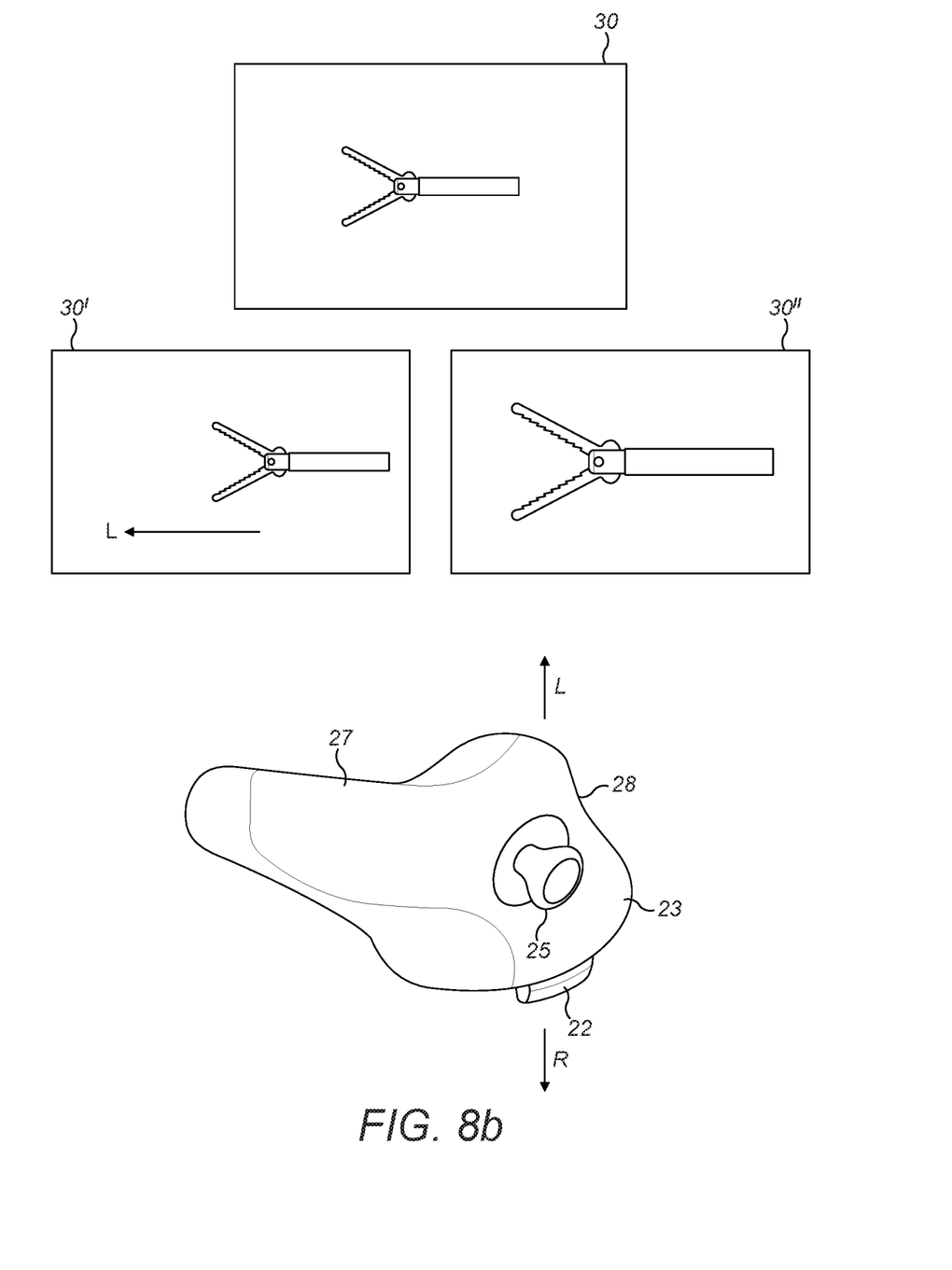
FIG. 8b shows an alternative view of the input of FIG. 5a with its operator selected frame of reference fixed to the display of FIG. 4.

FIG. 8*b* illustrates another example in which the input device 21*a* is being held by the operator O such that it is pointed 90 degrees to the right of the screen of display 30. If the operator O chooses to set their preferred frame of reference to be the same as the input frame once more, manipulating the input 25 to move left in respect to the body of the input device 21*a*, in the direction indicated by letter L in FIG. 8*b*, would result in a leftward movement of the distal end of the endoscope 41*c*, resulting in the displayed image of the instrument end effector 41*a* to shift to the right side of the captured image as shown on display 30'.

However, operator O could choose to set their preferred frame of reference to be with respect to the screen. In this example, moving the input 25 in the direction indicated by letter L in FIG. 8*b* would result in a forwards movement of the distal end of the endoscope 41*c*, resulting in the displayed image of the instrument end effector 41*a* appearing to be larger as shown on display 30". Alternatively, the operator O may choose another desired frame of reference.

Functional Input

The examples above describe the use of the input 25 for providing three-dimensional motion of the image capture device (e.g. endoscope 41*c*). The following examples describe the use of the input 25 for providing functional input to the system 10.

The system 10 provides for selectively permitting operative association between the input device(s) 21*a*, 21*b* and any of the instrument end effectors 41, 41*b*. In many surgical procedures, it is desirable for the operator to be able to select from among two or more instrument end effectors 41a, 41b. For example, the input device 21a, 21b is usable to control a plurality of instrument end effectors 41a, 41b. The input device 21a, 21b is usable to control one instrument end effector 41, 41b when operatively coupled to the one instrument end effector 41, 41b, and is usable to control another instrument end effector 41a, 41b when operatively coupled to that other instrument. In other words, an input device 21a, 21b is usable to control the instrument end effector 40a, 40b to which it is operatively coupled in an engaged mode. The coupling between input device 21a, 21b and instrument end effector 41a, 41b is changeable. One instrument end effector 41a can be controlled by a plurality of input devices 21a, 21b. The instrument end effector 41a is couple-able to one input device 21a to permit control of the instrument end effector 41a by the one input device 21a. Once decoupled from the one input device 21a, the instrument end effector 41a is couple-able to another input device 21b to permit control of the instrument end effector 41a by the other input device 21b. Thus, more than one instrument end effector 41a, 41b can be operatively associated with a single input device 21.

The input devices 21a, 21b are associable with, or operatively coupleable to, one instrument end effector 41a, 41b at a time. This association or coupling is, in one example, effected in software control. The operator O selects the desired coupling, for example by manipulating the respective input device 21a, 21b to select the respective instrument end effector 41a, 41b, such as by using the input 25 to select an option from a menu in an interface. Once a suitable instrument end effector 41a, 41b has been selected it is operably engaged/coupled with the input device 21a, 21b to provide the operator O with control over that chosen instrument end effector. This can be done using the clutch input 22 of the input device 21. However, the input device 21a, 21b itself need not be used to make this engagement. Another button or control, such as a foot pedal or switch on the operator console 20, can be used instead of, or as well as, the input device 21a, 21b. Alternatively, another button or control on the input device 21a, 21b other than clutch input 22 could be provided as an engagement input for operably engaging/coupling a suitable instrument end effector 41a, 41b with the input device 21a, 21b to provide the operator O with control over that chosen instrument end effector. This provides flexibility in the selection of the instrument end effector 41a, 41b. The instrument end effector 41a, 41b that is operatively coupled to the input device 21a, 21b can be termed an engaged instrument end effector. Instrument end effectors 41a, 41b that are not operatively coupled to an input device 21a, 21b can be termed disengaged instrument end effectors. A disengaged instrument end effector is not being actively controlled by an input device 21a, 21b. Suitably the processor 61 is configured to determine which of the instrument end effectors 41a, 41b is an engaged instrument.

Thus, the processor 61 can operate in a number of modes, namely in an engaged mode, in a disengaged mode, in an operational mode, and in a selection mode. In the engaged mode, the input device 21a, 21b is operatively coupled with an instrument end effector 41a, 41b. In the disengaged mode, the input device 21a, 21b is operatively decoupled from an instrument end effector 41a, 41b. The same mechanism described above to operatively couple an instrument end effector to an input device 21a, 21b can be used to operatively decouple that instrument end effector from that input device 21a, 21b. For example, the clutch input 22 of the input device 21a, 21b can be used to operatively decouple the associated instrument end effector 41a, 41b. Again, the input device 21a, 21b itself need not be used to effect this disengagement. Another button or control, such as a foot pedal or switch on the operator console 20, can be used instead of, or as well as, the input device 21a, 21b. Again, another button or control on the input device 21a, 21b other than clutch input 22 could be alternatively provided as an engagement input for operably disengaging/decoupling the associated instrument end effector 41a, 41b from the input device 21a, 21b. Once the previous instrument end effector has been operatively decoupled from the input device 21a, 21b, a different instrument end effector can be selected and operatively coupled to the input device 21a, 21b to provide the operator O with control over that chosen instrument.

In the selection mode, the processor 61 could further be configured such that upon disengagement of an instrument 40a, 40b from an input device 21, the input 25 of that input device 21a, 21b ceases to act as a three-dimensional input and automatically becomes an instrument end effector selection device to allow the operator O to select another instrument end effector for association with the input device 21a, 21b. In one example, when more than one input device 21a, 21b is being used, disengaging one of the input devices 21a, 21b results only in the disengagement of the associated instrument end effector of that input device 21a, 21b with the input 25 of the disengaged input device 21a, 21b turning into a selection device. Thus, the processor can concurrently operate in the disengaged and the selection modes. In another example, when more than one input device 21a, 21b is being used, disengaging one of the input devices 21a, 21b results in disengagement of all the associated instrument end effectors and the input 25 of all the input devices 21a, 21b automatically turn into selection devices.

As described earlier, the input 25 of one or more input devices 21a, 21b could also be used to control the various degrees of freedom (up/down, left/right, zoom in/out and roll) of the image capture device (e.g. endoscope 41c). This may occur in the operational mode, where for example, input 25 of a first input device 21a is operatively coupled to the endoscope 41c to control its up/down and left/right movements and input 25 of a second input device 21b can be operatively coupled to the endoscope 41c to control the zoom in/out and roll of the endoscope 41c. The clutch input 22 of the input device 21a, 21b can be used to cause the processor 61 to enter the operational mode and provide the operator O with control over the endoscope's required degrees of freedom. Alternatively, another engagement input of the input device 21a, 21b as described above or another button or control, such as a foot pedal or switch on the operator console 20, can be used instead of or as well as the clutch input 22 to cause the processor 61 to enter the operational mode. In one example, when either one of the input devices 21a, 21b are disengaged from their associated instrument end effector 41a, 41b while the other remains engaged to their associated instrument end effector 41a, 41b then both inputs 25 of the input devices 21a and 21b are disengaged from controlling the endoscope's degrees of freedom by the processor 61 and both inputs 25 become instrument selection devices.

As well as providing the operator with an instrument selection device, inputs 25 can be adapted to provide other functional input to the system 10 (e.g. the selection of a number of other available modes that may be accessible to the operator via a menu-type interface). In one example, when the system 10 enters these other functional modalities, the processor 61 is configured to disengage all input devices 21a, 21b from their respective associated instrument end effectors 41a, 41b. Furthermore, the processor 61 is configured to disengage all inputs 25 from the endoscope 41c.

While the present invention has been described in the context of a surgical robotic system, it must be appreciated that different aspects of this invention equally apply to other master-slave robotic systems. Thus, the robotic system may be an industrial system or another type of system. The robot could be an industrial robot or a robot for another function. The instruments could be an industrial or other form of tool. The body of the instrument could comprise a coupling for releasable attachment to a robot and an elongate shaft running between the coupling and the end effector.

The control processes described herein could be performed by one or more physical processing units executing software that causes the unit(s) to perform the control processes. The or each physical processing unit could be any suitable processor, such as a CPU or fixed function or programmable hardware.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A master-slave system comprising:
a first manipulator supporting a first end effector having multiple degrees of freedom;
a second manipulator supporting a second end effector;
an input device configured to concurrently receive from a hand of an operator a first master movement command to effect a desired slave movement of the first end effector and a second master movement command to effect a desired slave movement of the second end effector, wherein the input device comprises a first input for receiving the first master movement command;
a second input device configured to concurrently receive from a hand of an operator a third master movement command to effect a desired slave movement of a third end effector and a fourth master movement command to effect a desired slave movement of the first end effector, wherein the second input device comprises a second input for receiving the fourth master movement command; and
a processor configured to determine a desired slave movement of the first and the second end effectors in response to the first and second master movement commands received from the input device respectively, wherein the processor is configured to selectively associate at least one of the degrees of freedom of the first end effector with the first input and to effect movement of the at least one of the degrees of freedom of the first end effector in response to movement of the first input, and wherein the processor is configured to selectively associate at least one other of the degrees of freedom of the first end effector with the second input and to effect movement of the at least one other of the degrees of freedom of the first end effector in response to movement of the second input.

2. The system of claim 1, wherein the input device comprises a body for being held by the operator, the body being configured to be gripped in normal use by a single hand of the operator.

3. The system of claim 1, wherein the processor is operable in a plurality of modes comprising:
an engaged mode, wherein the input device is operatively coupled with the second end effector;
a disengaged mode, wherein the input device is operatively decoupled from the second end effector;
an operational mode, wherein the first input is operably coupled with the first end effector; and
a selection mode, wherein the first input is operably decoupled from the first end effector.

4. The system of claim 3, wherein the processor is configured to operate in the disengaged mode in response to a signal received from a clutch input.

5. The system of claim 3, wherein when the processor is in the engaged mode the input device is configured to receive the second master movement command to effect the desired slave movement of the second end effector.

6. The system of claim 3, wherein when the processor is in the operational mode the first input is configured to receive the first master movement command to effect the desired slave movement of the first end effector.

7. The system of claim 3, wherein when the processor is in the selection mode the first input is further configured to select a fourth end effector for association with the input device.

8. The system of claim 7, wherein
the processor is further configured to operate in the operational mode in response to receiving a signal from a second input and
the input device is further configured to receive a fifth master movement command to effect a desired slave movement of the fourth end effector in response to selection of the fourth end effector by the first input.

9. The system of claim 3, wherein the processor is further configured to operate in the operational mode in response to receiving a signal from a third input.

10. The system of claim 3, wherein when the processor enters the disengaged mode the processor is further configured to concurrently operate in the disengaged mode and the selection mode.

11. The system of claim 1, wherein the input device further comprises one or more of:
a drive mechanism coupled to the first input, the drive mechanism being configured to apply a force to the first input for providing force feedback to the operator;
a force sensor configured to sense a force applied to the first input for determining that a command is being received at the first input from the operator;
a capacitive sensor configured to sense when the operator is touching the first input for determining that a command is being received at the first input from the operator; and
a position sensor configured to sense the position of the first input relative to the body for determining that a command is being received at the first input from the operator.

12. The system of claim 1, wherein the processor is further configured to effect movement of one or more of:
the first end effector in accordance with the determined desired slave movement of the first end effector; and the second end effector in accordance with the determined desired slave movement of the second end effector.

13. The system of claim 1, wherein the first end effector comprises an image capture device for capturing an image of a worksite.

14. The system of claim 13, wherein the image capture device is an endoscope.

15. The system of claim 13, further comprising a display for displaying the captured image.

16. The system of claim 1, wherein the processor is further configured to determine the desired slave movement of the first end effector according to movement of the first input with respect to an operator selected frame of reference.

17. The system of claim 16, wherein the operator selected frame of reference is fixed to the input device; or
fixed to the display.

18. The system of claim 1, wherein the processor is further configured to continuously update a mapping between an input device frame of reference and a second end effector frame of reference and to continuously update a mapping between a first input frame of reference and a first end effector frame of reference such that movements of the first and second end effectors as displayed on the display correspond to the movements of the first input and the input device respectively.

* * * * *